US008569325B2

(12) United States Patent
Asai et al.

(10) Patent No.: US 8,569,325 B2
(45) Date of Patent: *Oct. 29, 2013

(54) METHOD OF TREATMENT WITH COADMINISTRATION OF ASPIRIN AND PRASUGREL

(75) Inventors: Fumitoshi Asai, Nishitokyo (JP); Atsuhiro Sugidachi, Kawasaki (JP); Taketoshi Ogawa, Tokyo (JP); Teruhiko Inoue, Ube (JP)

(73) Assignees: Daiichi Sankyo Company, Limited, Tokyo (JP); Ube Industries, Ltd., Yamaguchi (JP)

( * ) Notice: Subject to any disclaimer, the term of this patent is extended or adjusted under 35 U.S.C. 154(b) by 816 days.

This patent is subject to a terminal disclaimer.

(21) Appl. No.: 12/006,546

(22) Filed: Jan. 3, 2008

(65) Prior Publication Data

US 2008/0108589 A1 May 8, 2008

Related U.S. Application Data

(60) Division of application No. 10/600,266, filed on Jun. 20, 2003, which is a continuation of application No. PCT/JP01/11201, filed on Dec. 20, 2001.

(30) Foreign Application Priority Data

Dec. 25, 2000 (JP) .................. 2000-392983

(51) Int. Cl.
A01N 43/42 (2006.01)
A61K 31/44 (2006.01)
(52) U.S. Cl.
USPC ............................ 514/279; 514/443; 514/183
(58) Field of Classification Search
None
See application file for complete search history.

(56) References Cited

U.S. PATENT DOCUMENTS

| | | | |
|---|---|---|---|
| 2,890,240 A | 6/1959 | Hamer et al. | |
| 3,235,583 A | 2/1966 | Edmunds | |
| 4,080,447 A | 3/1978 | Amselem | |
| 4,104,390 A | 8/1978 | Ferrand et al. | |
| 4,147,787 A | 4/1979 | Maffrand | |
| 4,193,997 A | 3/1980 | Boigegrain et al. | |
| 4,321,266 A | 3/1982 | Amselem et al. | |
| 4,400,384 A | 8/1983 | Amselem et al. | |
| 4,500,534 A | 2/1985 | Frehel et al. | |
| 4,515,951 A | 5/1985 | Boigegrain et al. | |
| 4,529,596 A | 7/1985 | Aubert et al. | |
| 4,537,894 A | 8/1985 | Blanchard et al. | |
| 4,740,510 A | 4/1988 | Badore et al. | |
| 5,190,938 A | 3/1993 | Badore et al. | |
| 5,288,726 A | 2/1994 | Koike et al. | |
| 5,401,730 A | 3/1995 | Sauvage et al. | |
| 5,874,581 A | 2/1999 | Ataka et al. | |
| 5,989,578 A | 11/1999 | Bernat et al. | |
| 6,248,729 B1 | 6/2001 | Coniglio et al. | |
| 6,509,348 B1 | 1/2003 | Ogletree | |
| 6,642,252 B2 | 11/2003 | Bisacchi et al. | |
| 6,670,386 B2 | 12/2003 | Sun et al. | |
| 6,693,115 B2 | 2/2004 | Asai et al. | |
| 6,706,720 B2 | 3/2004 | Atwal et al. | |
| 2005/0203122 A1 | 9/2005 | Doser et al. | |
| 2008/0300409 A1 | 12/2008 | Finkelstein et al. | |
| 2008/0306268 A1 | 12/2008 | Finkelstein et al. | |
| 2009/0187022 A1 | 7/2009 | Finkelstein et al. | |
| 2011/0003847 A1 | 1/2011 | Doser | |

FOREIGN PATENT DOCUMENTS

| | | |
|---|---|---|
| CA | 1147658 | 6/1983 |
| EP | 0 542 411 A2 | 5/1993 |
| EP | 0 555 042 | 8/1993 |
| EP | 0 573 975 | 12/1993 |
| EP | 0 641 770 | 3/1995 |
| EP | 1 298 132 A1 | 4/2003 |
| EP | 1 350 511 A1 | 10/2003 |
| EP | 1 350 511 B1 | 9/2008 |
| FR | 2 596 392 | 10/1987 |
| FR | 2 597 102 | 10/1987 |
| GB | 1445524 | 8/1976 |
| GB | 1501797 | 2/1978 |
| GB | 1561504 | 2/1980 |
| GB | 2469883 | 11/2010 |
| HU | P1991 03745 | 12/1991 |
| HU | P1991 03746 | 12/1991 |
| JP | 6-41139 | 2/1994 |
| JP | 6-271582 | 9/1994 |
| JP | 8-291117 | 11/1996 |
| JP | 11-510818 | 9/1999 |
| JP | 2000-266780 | 4/2000 |
| JP | 2000-205396 | 6/2000 |
| JP | 2000-205396 | 7/2000 |

(Continued)

OTHER PUBLICATIONS

Asai, Fumitoshi et al., "Platelet inhibitory activity and pharmacokinetics of prasugrel (CS-747) a novel thienopyridine P2Y12 inhibitor: A single ascending dose study in healthy humans," Platelets, vol. 17, No. 4, pp. 209-217, Jun. 2006.

Herbert, J.M. et al., "The anti-aggregating and antithrombotic activity of ticlopidine is potentiated by aspirin in the rat," Thromb. Haemost., vol. 76, pp. 94-98, 1996.

(Continued)

Primary Examiner — Jeffrey S. Lundgren
Assistant Examiner — Meghan Finn
(74) Attorney, Agent, or Firm — Kenneth H. Sonnenfeld; Wan Chieh Lee; King & Spalding LLP

(57) ABSTRACT

A method for the prevention of diseases caused by thrombus or embolus. The method is to separately administer 2-acetoxy-5-(α-cyclopropylcarbonyl-2-fluorobenzyl)-4,5,6,7-tetrahydrothieno[3,2-c]pyridine or a pharmaceutically acceptable salt thereof, and aspirin, in their pharmacologically effective amounts, to a warm-blooded animal.

26 Claims, No Drawings

(56) References Cited

FOREIGN PATENT DOCUMENTS

| JP | 2000-266780 | 9/2000 |
|---|---|---|
| JP | 2002-145883 | 5/2002 |
| WO | WO 97/29753 A1 | 8/1997 |
| WO | WO 00/061537 | 10/2000 |
| WO | WO 00/061541 | 10/2000 |
| WO | WO 00/66130 | 11/2000 |
| WO | WO 2009/130289 | 10/2009 |

OTHER PUBLICATIONS

Herbert, J.M. et al., "The anti-aggregating and antithrombotic activity of clopidogrel is potentiated by aspirin in several experimental models in the rabbit," Thromb. Haemost., vol. 80, pp. 512-518, 1998.
Jakubowski, J.A. et al., "A multiple dose study of prasugrel (CS-747), a novel thienopyridine P2Y12 inhibitor, compared with clopidogrel in healthy humans," British Journal of Clinical Pharmacology, vol. 63, No. 4, pp. 421-430, Oct. 31, 2006 (online publication).
Jernberg, Tomas et al., "Prasugrel achieves greater inhibition of platelet aggregation and a lower rate of non-responders compared with clopidogrel in aspirin-treated patients with stable coronary artery disease," European Heart Journal, vol. 27, pp. 1166-1173, 2006.
Matsushima, Nobuko et al., "Platelet inhibitory activity and pharmacokinetics of prasugrel (CS-747) a novel thienopyridine P2Y12 inhibitor: A multiple-dose study in healthy humans," Platelets, vol. 17, No. 4, pp. 218-226, Jun. 2006.
Weerakkody, Govinda J. et al., "Comparison of Speed of Onset of Platelet Inhibition After Loading Doses of Clopidogrel Versus Prasugrel in Healthy Volunteers and Correlation With Responder Status," Am J Cardiol, vol. 100, pp. 331-336, 2007.
U.S. Appl. No. 10/600,266, filed Jun. 20, 2003, Fumitoshi Asai et al.
U.S. Appl. No. 11/520,168, filed Sep. 13, 2006, Fumitoshi Asai et al.
S. Uchiyama et al., Combination therapy with low-dose aspirin and ticlopidine in cerebral ischemia, Stroke, Dec. 1989, vol. 20, No. 12, pp. 1643-1647.
Sugidachi et al., "The in vivo pharmacological profile of CS-747, a novel antiplatelet agent with platelet ADP receptor antagonist properties", British Journal of Pharmacology, 2000, vol. 209, No. 7, pp. 1439 to 1446.
Database CA on STN, AN.133:187474, Asai, Fumitoshi et al., CS-747, a new platelet ADP receptor antagonist Annual Report of Sankyo Research Laboratories, 1999, vol. 51, pp. 1 to 44, abstract.
Saniabadi AR et al., "Effect of dipyridamole alone and in combination with aspirin on whole blood platelet aggregation, PGI2 generation, and red cell deformability ex vivo in man", Cardiovascular Research, 1991, vol. 25, No. 3, pp. 177 to 183.
J. Cardiovasc. Pharmacol., vol. 49, No. 3, Mar. 2007, p. 167-173.
Seminars in Thrombosis and Hemostasis, vol. 31, No. 2, 2005, p. 184-194.
Akyuz et al., "The effect of aspirin, ticlopidine and their low-dose combination on platelet aggregability in acute ischemic stroke: a short duration follow-up study," Eur. J. Neurol., 6(1):57-61 (1999).
Asai et al., "Antithrombotic and Antiplatelet Effects of CS-747, A Novel P2Y Antagonist," Thromb. Haemost. 1999 (Supp) p. 829.
Born et al., "Aspirin versus clopidogrel: the wrong question?" The Lancet, 349, 1997, p. 806-7, Mar. 15, 1997.
Chapter 52 of Heart Disease, 6$^{th}$ ed., by Goldhaber, pp. 1902-1903, 2001.
Clagette et al., "Prevention of Venous Thromboembolism," Chest, 114: 531S-560S, 1998.
Chen et al., "Aspirin resistance is associated with a higher incidence of myonecrosis after nonurgent percutaneous coronary intervention despite clopidogrel pretreatment," J Am Coll Cardiol, 43:1122-6, 1125 (2004).
Cure Trial Investigators, "Effects of Clopidogrel in Addition to Aspirin in Patients with Acute Coronary Syndromes without ST-Segment Elevation," NEJM, 345(7):494-502 (2001).
CURE Study Investigators, "The Clopidogrel in Unstable angina to prevent Recurrent Events (CURE) trial programme: Rationale, design and baseline characteristics including a meta-analysis of the effects of thienopyridines in vascular disease," Eur. Heart Journal, 21(24):2033-2041 (Dec. 1, 2000).
European Opposition by Helm AG filed Jun. 4, 2009 against European Patent No. 1 350 511, which issued from European Application No. 01271850.8, with English translation of non-English filings.
European Opposition by Teva Pharmaceutical Industries filed Jun. 9, 2009 against European Patent No. 1 350 511, which issued from European Application No. 01271850.8.
Farrell et al., "The lack of augmentation by aspirin of platelet reactivity by ticlopidine," Am J Cardiol., 83(5):770-774 (1999).
FDA Cardiovascular and Renal Drugs Advisory Committee, Slide Presentation and Transcript of Meeting, Feb. 3, 2009, available at <<http://www.fda.gov/AdvisoryCommittees/CommitteesMeetingMaterials/Drugs/CardiovascularandRenalDrugsAdvisoryCommittee/ucm125999.htm>>.
Goodman and Gilman, The Pharmacological Basis of Therapeutics, Fifth Edition, Macmillan Publishing Co., Inc., p. 25-26, 1975.
Henke, P.K., "Commentary," Perspectives in Vascular Surgery and Endovascular Therapy, 20(2):223-224 (2008).
Ikeda, "Preface: Antiplatelet Therapy—An Update," Haemostasis, vol. 30, Suppl. 3, 2000, p. 1.
Indian Opposition filed Jan. 30, 2009 against Indian Patent No. 214103, which issued from Indian Application No. 777/KOLNP/2003; Affidavit dated Jul. 2, 2009 supporting Opposition; and Affidavit dated Nov. 16, 2009 in support of Indian patent.
Jarvis et al., "Clopidogrel: A Review of its Use in the Prevention of Atherothrombosis," Drugs, 60(2):347-377, Aug. 2000, Abstract.
Kolansky et al., "Combination Therapy with Clopidogrel and Aspirin After Coronary Stenting," Catheter Cardiovasc Interv., vol. 50, 276-279 (2000).
Leon et al., "A Clinical Trial Comparing Three Antithrombotic-drug Regimens After Coronary-Artery Stenting," New England Journal of Medicine, vol. 339, No. 23, pp. 1665-1671, Dec. 3, 1998. (M&C sent letter to Israel associate listing this reference on Jun. 8, 2005; copied to us in Feb. 2010; DaiichiSankyo provided copy to us on Feb. 25, 2010).
Lev et al., "Aspirin and Clopidogrel Drug Response in Patients Undergoing Percutaneous Coronary Intervention," Journal of the American College of Cardiology, 47(1):27-33 (2006).
Lipton et al., "Adjuvant antiplatelet therapy with aspirin in colorectal cancer," J. Med. 13(5-6): 419-429, 1982.
Martindale, "The Extra Pharmacopeia," 31$^{st}$ edition, pp. 17-22, 1996.
Moussa, "Effectiveness of Clopidogrel and Aspirin Versus Ticlopidine and Aspirin in Preventing Stent Thrombosis After Coronary Stent Implantation," Circulation, 99, 2364-2366, May 11, 1999.
Müller et al., "A Randomized Comparison of Clopidogrel and Aspirin Versus Ticlopidine and Aspirin After the Placement of Coronary-Artery Stents," Circulation; vol. 101, pp. 590-593, 2000.
PLAVIX® Prescribing Information, "Dosage and Administration," revised May 2009.
Prescribing Label for Lovenox approved by the FDA on Nov. 17, 2000.
Presentation to the Cardiovascular and Renal Drugs Advisory Committee, Feb. 3, 2009, Slide # 26 (http://www.fda.gov/AdvisoryCommittees/CommitteesMeetingMaterials/Drugs/CardiovascularandRenalDrugsAdvisory Committee/ucm125999.htm).
Press Release of Eli Lilly and Sankyo of Dec. 21, 2000, Chemie.DE Information Service.
Quinn et al., "Ticlopidine and Clopidogrel," Circulation, vol. 100, 1667-1672, Oct. 12, 1999. (M&C sent letter to Israel associate listing this reference on Jun. 8, 2005; copied to us in Feb. 2010; copy from Daiichi Sankyo on Feb. 25, 2010).
Response to Notices of Opposition for European Patent No. 1 350 511, which issued from European Application No. 01271850.8, dated Mar. 26, 2010.
Rupprecht et al., "Comparison of Antiplatelet Effects of Aspirin, Ticlopidine, or Their Combination After Stent Implantation," Circulation, 1998, 97, pp. 1046-1052.
Sacco et al., "Update on Antiplatelet Therapy for Stroke Prevention," Arch. Intern. Med., 160, Jun. 12, 2000, 1579-1582, Abstract.

(56) References Cited

OTHER PUBLICATIONS

Savi et al., "Identification and Biological Activity of the Active Metabolite of Clopidogrel," Thromb. Haemost, 2000, 84, pp. 891-896.
Steinhubl, "Antiplatelet Agents in Cardiology: The Choice of Therapy," Ann. Thorac. Surg, 70:S3-8, 2000, presented Jan. 22-23, 1999.
TICLID® Prescribing Information, revised Mar. 2001.
Uzun et al., "The effects of heparin on DLD-1 colon cancer cell line," Bratisl Lek Listy, 110(1), 3-6, 2009.
Van de Graaff, "Antiplatelet medications and their indications in preventing and treating coronary thrombosis," Annals of Medicine, 32(8), Nov. 2000, p. 561-571, Abstract.
Van de Graaff et al., "Variable Interindividual Responses to Antiplatelet Therapies—Do They Exist, Can We Measure Them, and Are They Clinically Relevant?" Heart Drug, 1(1):35-43 (2001), available online Aug. 2000.
Worrell et al., "Antiplatelet Therapy in Secondary Stroke Prevention," Current Atherosclerosis Reports, 2(2):104-109 (Mar. 2000).
Yende et al., "Effect of clopidogrel on bleeding after coronary artery bybass surgery," Crit. Care Med., 29(12):2271-2275 (2001).
Aino Lepantalo, "Individual Variation in in vitro Efficacy of Antiplatelet Medication," Dissertation, 2007.
Alexander et al., "Prior Aspirin Use Predicts Worse Outcomes in Patients with Non-ST-Elevation Acute Coronary Syndromes," The American Journal of Cardiology, 84: 1147-1151, Apr. 15, 1999.
Antman et al., "Early and Late Benefits of Prasugrel in Patients with Acute Coronary Syndromes Undergoing Percutaneous Coronary Intervention," Journal of American College of Cardiology, 51(21):2028-2033, Nov. 21, 2008.
"Aspirin Ineffective for Primary Prevention in Patients with Diabetes," MeReC Monthly No. 9, Dec. 2008, <<http://www.npc.co.uk/ebt/merec/cardio/diabetes2/merec_monthly_no9.html.
Clarke et al., "The Metabolism of Clopidrogrel is Catalyzed by Human Cytochrome P450 3A and is Inhibited by Atorvastatin," The American Society for Pharmacology and Experimental Therapeutic, 31(1):53-59, 2003.
"Collaborative Meta-Analysis of Randomised Trials of Antiplatelet Therapy for Prevention of Death, Myocaridal Infarction, and Stroke in High Risk Patients," BMJ, 324:71-86; Jan. 12, 2002.
Erlinge et al., "Patients with Poor Responsiveness to Thienopyridine Treatment or With Diabetes Have Lower Levels of Circulating Active Metabolite, but their Platelets Respond Normally to Active Metabolite Added Ex Vivo," Journal of Amercan College of Cardiology, 52(24):1968-1977, Nov. 24, 2008.
Fayer et al., "Interactions of Two Major Metabolites of Prasugrel, A Thienopyridine Antiplatelet Agent With the Cytochromes P450," The American Society for Pharmacology and Experimental Therapeutics, 34(4):600-607, 2006.
Ferguson et al., "Aspirin and Clopidogrel Response Variability," Texas Heart Institute Journal, 35(3):313-320, Nov. 3, 2008.
Jaremo et al., "Individual Variations of Platelet Inhibition after Loading Doses of Clopidogrel," Journal of Internal Medicine, 252: 233-238, 2002.
Lau et al., "Contribution of Hepatic Cytochrome P450 3A4 Metabolic Activity to the Phenomenon of Clopidogrei Resistance," Circulation, 109(2)166-171, Jan. 20, 2004, Abstract only.
Murphy et al., "Reduction in Recurrent Cardiovascular Events with Prasugrel Compared with Clopidogrel in Patients with Acute Coronary Syndromes from the TRITON-TIMI 38 Trial," European Heart Journal, 29:2473-2479, 2008.
Payne et al., "Increased Active Metabolite Formation Explains the Greater Platelet inhibition with Prasurgel Compared to High-Dose Clopidrogel," J. Cardiovasc. Pharmacol., 50(5):555-562, Nov. 2007.
Payne et al., "Switching Directly to Prasugrel from Clopidogrel Results in Greater Inhibition of Platelet Aggregation in Aspirin-Treated Subjects," Platelets, 19(4):275-281, Jun. 2008.
"Platelet Aggregation in Cancer," J. Biol. Chem, 2007, abstract 282, 25993-26001.

Reinhart et al., "Prasugrel: A Critical Comparison with Clopidrogel," Pharmacotherapy, 29(12):1441-1451, 2009.
Response to the Submission of the Patent Proprieter (Daiichi, Ube) of Mar. 26, 2010 for European Patent No. 1 350 511, which issued from European Application No. 01271850.8, dated Jun. 9, 2010.
Reuters Health Information, "Clopidogrel Resistance Does not Predict Response to Ticlopidine," J. Am. Coll. Cardiol., 50:1132-1137, 2007.
Thebault et al., "Repeated-Dose Pharmacodynamics of Clopidogrel in Healthy Subjects," Seminars in Thombosis and Hemostasis, 25(2): 9-14, 1999.
Wallentin et al., "Prasugrel Achieves Greater and Faster $P2Y_{12}$ Receptor-Mediated Platelet Inhibition than Clopidogrel due to More Efficient Generation of Its Active Metabolite in Aspirin-Treated Patients with Coronary Artery Disease," European Heart Journal, 29:21-30, 2008.
Wiviott et al., "Greater Clinical Benefit of More Intensive Oral Antiplatelet Therapy with Prasugrel in Patients with Diabetes Mellitus in the Trial to Assess Improvement in Therapeutic Outcomes by Optimizing Platelet Inhibition with Prasugrei-Thrombolysis in Myocardial Infarction 38," Circulation, 1626-1636, Oct. 14, 2008.
Wiviott et al., "Intensive Oral Antiplatelet Therapy for Reduction of Ischaemic Events including Stent Thrombosis in Patients with Acute Coronary Syndromes Treated with Percutaneous Coronary Intervention and Stenting in the TRITON-TIMI 38 Trial: a Subanalysis of a Randomised Trial," <<www.theLancet.comn>>, 1-11, Mar. 29, 2008.
Wiviott et al., Prasugrel versus Clopodogrel in Patients with Acute Coronary Syndromes, The New England Journal of Medicine, 357(20): 2002-2015, Nov. 15, 2007.
Wiviott et al., "Prasugrel Compared with High Loading- and Maintenance-Dose Clopidogrel in Patients with Planned Percutaneous Coronary Intervention," Circulation, 2923-2932, Dec. 2007.
Wiviott et al., "Randomized Comparison of Prasugrel (CS-747, LY640315), a Novel Thienopyridine $P2Y_{12}$ Antagonist, With Clopidogrel in Percutaneous Coronary Intervention," Circulation, 3366-3373, Jun. 28, 2005.
Algaier et al., "Interaction of the Active Metabolite of Prasugrel, R-138727, with Cysteine 97 and Cysteine 175 of the Human $P2Y_{12}$ Receptor," Journal of Thrombosis and Haemostasis, 6, pp. 1908-1914, 2008.
Allender et al., European Cardiovascular Disease Statistics, 2008 Edition, pp. 1-112.
Angiolillo et al., "Increased Platelet Inhibition After Switching From Maintenance Clopidogrel to Prasugrel in Patients with Acute Coronary Syndromes," Journal of the American College of Cardiology, 56(13), pp. 1017-1023, 2010.
Armstrong et al., "In the Presence of Strong $P2Y_{12}$ Receptor Blockade, Aspirin Provides Little Additional Inhibition of Platelet Aggregation," Journal of Thrombosis and Haemostasis, 9, pp. 552-561, 2011.
Asai et al., "A Comparison of Prasugrel (CS-747, LY640315) With Clopidogrel on Platelet Function in Healthy Male Volunteers," Oral Contributions—Features Oral Session . . . Platelet Resistance: Importance, Detection, and Treatment, Abstract No. 868-B, Mar. 9, 2005, JACC, Abstracts—Angiograophy & Interventional Cardiology, pp. 86A-90A, Feb. 1, 2005.
Becker et al., "Synthesis, SAR and In Vivo Activity of Novel Thienopyridine Sulfonamide Pyrrolidinones as Factor Xa Inhibitors," Bioorganic & Medicinal Chemistry Letters, 9, pp. 2753-2758, 1999.
Bertilsson, "Geographical/Interracial Differences in Polymorphic Drug Oxidation: Current State of Knowledge of Cytochromes P450 (CYP) 2D6 and 2C19," Clinical Pharmakinetics, 29(3), pp. 192-209, Sep. 1995, Abstract only.
Bhatt et al., "Clopidogrel and Aspirin versus Aspirin Alone for the Prevention of Atherothrombotic Events," The New England Journal of Medicine, 354(16), pp. 1706-1717, Apr. 20, 2006.
CAPRIE Steering Committee, "A Randomised, Blinded, Trial of Clopidogrel Versus Aspirin in Patients at Risk of Ischaemic Events (CAPRIE)," The Lancet, 348, pp. 1329-1339, Nov. 16, 1996.

(56) References Cited

OTHER PUBLICATIONS

COMMIT, "Addition of Clopidogrel to Aspirin in 45852 Patients With Acute Myocardial Infarction: Randomised Placebo-Controlled Trial," www.thelancet.com, 366, pp. 1607-1621, 2005.
Corr et al., "Managing Heart Disease Coronary Revascularization: Knife or Catheter?," European Heart Journal Supplements, pp. B43-B48, 2003.
Cosma et al., "Relationship Between Genotype and Function of the Human CYP1A1 Gene," Journal of Toxicology and Evironmental Health, part A, vol. 4, pp. 309-316, Oct. 1993 (Abstract Only).
Declaration of Dr. Joseph A. Jakubowski filed in the European Opposition Proceedings for EP 1 350 511, Jan. 1, 2011.
Declaration of Dr. Robert William Gristwood filed in the European Opposition Proceedings for EP 1 350 511, Jan. 19, 2011.
Declaration of Dr. Ian Boden Wilkinson filed in the European Opposition Proceedings for EP 1 350 511, Jan. 20, 2011.
Dovlatova et al., "The Reversible $P2Y_{12}$ Antagonist Cangrelor Influences the Ability of the Active Metabolites of Clopidogrel and Prasugrel to Produce Irreversible Inhibition of Platelet Function," Journal of Thrombosis and Haemostasis, 6, pp. 1153-1159, 2008.
Eisenstein et al., "Clopidrogel Use and Long Term Clinical Outcomes After Drug-Eluting Stent Implantation," JAMA, 297(2), pp. 159-168, 2007.
EMEA, "Assessment Report for Efient®," Procedure No. EMEA/H/C/000984, European Medicines Agency, Evaluation of Medicines for Human Use, EMEA/117561/2009, 2009.
Erlinge et al., "Patients with Poor Responsiveness to Thienopyridine Treatment and those With Diabetes Have Lower Levels of Circulating Active Metabolite, but their Platelets Respond Normally to Active Metabolite," 2008 Congress of the European Society of Cardiology, Abstract P3573, Aug. 30, 2008.
Fox et al., "The ENACT Study: a pan-European Survey of Acute Coronary Syndromes," European Heart Journal, 21, pp. 1440-1449, 2000.
Frelinger III, et al., "The Active Metabolite of Prasugrel Inhibits Adenosine Diphosphate- and Collagen-Stimulated Platelet Procoagulant Activities," J. of Thrombosis and Haemostasis, 6, pp. 359-365, 2007.
Frelinger III, et al., "Abstract 3293:The Active Metabolite of Prasugrel Inhibits Platelet Procoagulant Activities," Circulation, 114, p. 699, 2006, Abstract Only.
Frelinger III, et al., "The Active Metabolite of Prasugrel Inhibits ADP-Stimulated Thrombo-Inflammatory Markers of Platelet Activation: Influence of Other Blood Cells, Calcium, and Aspirin," Thrombosis Haemostasis, 98, pp. 192-200, 2007.
Geiger et al., "Specific Impairment of Human Platelet P2YAC ADP Receptor-Mediated Signaling by the Antiplatelet Drug Clopidogrel," Arterioscler Thomb Vasc Biol., pp. 2007-2011, Aug. 1999.
Giusti, "Response to Antiplatelet Treatment: From Genes to Outcome,"www.thelancet.com, pp. 1-3, Aug. 29, 2010.
Gryglewski et al., "Thombolysis by Thienopyridines and Their Congeners,"Journal of Physiology and Pharmacology, 51(4), pp. 683-693, 2000.
Harker et al., "Mechanism of Action of Dipyridamole," Thrombosis Research, pp. 39-46, 1983.
Hasegawa et al., "Stereoselective Inhibition of Human Platelet Aggregation by R-138727, the Active Metabolite of CS-747 (Prasugrel, LY640315), a Novel $P2Y_{12}$ Receptor Inhibitor," Thromb. Haemost., 94, pp. 593-598, 2005.
Hashimoto et al., "The Influence of $P2Y_{12}$ Receptor Deficiency on the Platelet Inhibitory Activities of Prasugrel in a Mouse Model: Evidence for Specific Inhibition of $P2Y_{12}$ Receptors by Prasugrel," Biochemical Pharmacology, 74, pp. 1003-1009, 2007.
Hirota et al., "Efficacy of CS-747, A New Potent Antiplatelet Agent," Clinical Pharmacology & Therapeutics, 65(2), p. 148, Feb. 1999.
Holmes et al., "ACCF/AHA Clopidogrel Clinical Alert: Approaches to the FDS Boxed Warning," Circulation, 122, pp. 537-557, 2010.
Ingall et al., "Antagonists of the Platelet $P_{2T}$ Receptor: A Novel Approach to Antithrombotic Therapy," J. Med. Chem., 42, pp. 213-220, 1999.
Judge et al., "Relationship between Degree of $P2Y_{12}$ Receptor Blockade and Inhibition of $P2Y_{12}$-Mediated Platelet Function," Thrombosis and Haemostasis, 103, pp. 1-8, 2010.
Kamishirado et al., "Randomized Comparison of Cilostazol Versus Ticlopidine Hydrochloride for Antiplatelet Therapy After Coronary Stent Implantation for Prevention of Late Restenosis," Am. Heart J., 144(2), pp. 303-308, 2002.
Karlberg et al., "Comparison of Three Independent Methods as Estimates of Platelet Inhibition After a Single Dose of Acetylsalicyclic Acid," Scand J. Clin. Lab. Invest., 53, pp. 835-841, 1993.
Kazui et al., "Mechanism for Production of Pharmacologically Active Metabolite of CS-747, A New Anti-Platelet Agent," vol. 16, Pharmacokinetics, pp. S78-S79, 2001.
L'Allier et al., "Clopidogrel 600-Mg Double Loading Dose Achieves Stronger Platelet Inhibition Than Conventional Regimens," Journal of the American College of Cardiology, 51(11), pp. 1066-1072, 2008.
Lepantalo, "Individual Variation in In Vitro Efficacy of Antiplatelet Medication," Coagulation Disorders Unit, Division of Hematology, Department of Medicine, Helsinki University Central Hospital, Finland and Department of Medicine, Institute o f Clinical Medicine, Faculty of Medicine, University of Helsinki, Finland, 2007.
Lopez-Farre et al., "Effects of Aspirin on Platelet-Neutrophil Interactions," Circulation, 91, pp. 2080-2088, 1995.
Mega et al., "Genetic Variants in ABCB1 and CYP2C19 and Cardiovascular Outcomes after Treatment with Clopidogrel and Prasugrel in the TRITON-TIMI 38 Trial: A Pharmacogenetic Analysis," www.theLancet.com, pp. 1-8, 2010.
Montalescot et al., "Prasugrel Compared with High-Dose Clopidogrel in Acute Coronary Syndrome," Thrombosis and Haemostasis, pp. 213-223, 2010.
Montalescot et al., "Prasugrel Compared with Clopidogrel in Patients undergoing Percutaneous Coronary Intervention for ST-Elevation Myocardial Infarction (TRITON-TIMI 38): Double-Blind, Randomised Controlled Trial," www.thelancet.com, 373, pp. 723-731, Feb. 28, 2009.
Niitsu et al., "Prasugrel (CS-747, LY640135) Hydrochloride, a Novel Thienopyridine Prodrug, Shows Potent Antiplatelet and Antithrombotic Effects with Rapid Onset of Action in Rats," Blood, 106, Abstract. 1879, p. 534A, 2005.
Niitsu et al., "Repeat Oral Dosing of Prasugrel, a Novel $P2Y_{12}$ Receptor Inhibitor, Results in Cumulative and Potent Antiplatelet and Antithrombotic Activity in Several Animal Species," European Journal of Pharmacology, 579, pp. 276-282, 2008.
Ogawa et al., "Greater In Vivo Potency of Prasugrel (CS-747 LY640315) vs. Clopidogrel is Not Explained by Differential Activity of Active Metabolites," European Heart Journal, 26, suppl. 1, poster presentation, slide No. 61, Abstr, P2954, 2005.
Peters et al., "Effects of Aspirin Dose When Used Alone or in Combination with Clopidogrel in Patients with Acute Coronary Syndrome: Observations From the Clopidogrel in Unstable Angina to Prevent Recurrent Events (CURE) Study," Circulation, pp. 1682-1687, 2003.
Prescribing Information—Effient, 2009.
Puma et al., "Thrombolytic, Antithrombin, and Antiplatelet Treatment of Acute Coronary Syndromes," J. Am. Osteopath Assoc., 100(1), pp. S8-S12, 2000.
Ratiopharm Submission for EP 1 350 511 filed Jan. 21, 2011.
Rauch et al., "Regulation of Functionally Active P2Y12 ADP Receptors by Thrombin in Human Smooth Muscle Cells and the Presence of P2Y12 in Carotid Artery Lesions," Arterioscler Thromb. Vasc. Biol., 30, pp. 2434-2442, 2010.
Reist et al., "Very Slow Chiral Inversion of Clopidogrel in Rats: A Pharmacokinetic and Mechanistic Investigation," Drug Metabolism and Disposition, 28(12), pp. 1405-1410, 2000.
Roden et al., "Responding to the Clopidogrel Warning by the US Food and Drug Administration, Real Life is Complicated," Circulation, 122, pp. 445-448, 2010.
Rothwell et al., "Effect of Daily Aspirin on Long-Term Risk of Death Due to Cancer: Analysis of Individual Patient Data from Radomised Trials,"www.Thelancet.com, pp. 1-11, 2010.

(56) References Cited

OTHER PUBLICATIONS

Sabatine et al., "Addition of Clopidogrel to Aspirin and Fibrinolytic Therapy for Myocardial Infarction with ST-Segment Elevation," The New England Journal of Medicine, 352(12), pp. 1179-1189 Mar. 24, 2005.
Savi et al., "The Antiaggregating Activity of Clopidogrel is Due to a Metabolic Activation by the Hepatic Cytochrome P450-1A," Thrombosis and Haemostasis, 72(2), pp. 313-317, 1994.
Schror et al., "Prasugrel, ein neues Thienopyridin," Homostaseologie, pp. 351-355, 2007.
Schwarz et al., "Flow Cytometry Analysis of Intracellular Vasp Phosphorylation for the Assessment of Activating and Inhibitory Signal Transduction Pathways in Human Platelets," Thomb. Haemost., 82, pp. 1145-1152, 1999.
Serebruany, "Lack of Outcome Benefit and Clopidogrel "resistance"—The Triton Trial Challenge," Thrombosis and Haemostasis, pp. 415-418, 2010.
Smith et al., "Abstract 10881: Mortality Benefit with Prasugrel in TRITON-TIMI 38 Coronary Artery Bypass Grafting (CABG) Cohort: Risk Adjusted Retrospective Data Analysis," Circulation, 122, A10881, 2010.
Spinier et al., "Review of Prasugrel for the Secondary Prevention of Atherothrombosis," J. Manag. Care Pharm., 15(5), pp. 383-395, 2009.
Steinhubl et al., "Attainment and Maintenance of Platelet Inhibition Through Standard Dosing of Abciximab in Diabetic and Nondiabetic Patients Undergoing Percutaneous Coronary Intervention," Circulation, pp. 1977-1982, Nov. 9, 1999.
Steinhubl et al., "Early and Sustained Dual Oral Antiplatelet Therapy Following Percutaneous Coronary Intervention," JAMA, 288(19), pp. 2411-2420, corrections on p. 987, Nov. 20, 2002.
Storey et al., "The Central Role of the $P_{2T}$ Receptor in Amplification of Human Platelet Activation, Aggregation, Secretion and Procoagulant Activity," British Journal of Haematology, 110, pp. 925-934, 2000.
Sugidachi et al., "Anti-Platelet and Anti-Thrombotic Effects of CS-747, a Novel $P2Y_{12}$ Receptor Antagonist, In Combination With Aspirin," NIA—Exhibition Area, Supplement to the Journal of Thrombosis and Haemostasis, Abstract P2032, Jul. 2003.
Sugidachi et al., Antiplatelet Action of R-99224, An Active Metabolite of a Novel Thienopyridine-Type $G_i$-Linked P2T Antagonist, CS-747, British Journal of Pharmacology, 132, pp. 47-54, 2001.
Sugidachi et al., "The Greater in vivo Antiplatelet Effects of Prasugrel as Compared to Clopidogrel Reflect More Efficient Generation of its Active Metabolite with Similar Antiplatelet Activity to that of Clopidogrel's Active Metabolite," Journal of Thrombosis and Haemostasis, 5, pp. 1545-1551, 2007.
Sugitachi et al., "Pharmacological Action of Prasugrel: Novel Platelet $P2Y_{12}$ Receptor Inhibitor," Cell, 39(14), pp. 30(607)-33(610), 2007 (with certified English translation).
Togni et al., "Percutaneous Coronary Interventions in Europe 1992-2001," European Heart Journal, 25, pp. 1208-1213, 2004.
Vane et al., "Cycooxygenases 1 and 2," Annu. Rev. Pharmacol. Toxicol., 38, pp. 97-120, 1998.
Varenhorst et al., "Abstract 3201: Greater P2Y12 Inhibition with Prasugrel Compared With Clopidogrel in Aspirin-Treated Patients Based on Higher Plasma Concentration of the Active Metabolite," Circulation, 116, pp. 719-720, 2007, Abstract Only.
Weber et al., "Specific Inhibition of ADP-Induced Platelet Aggregation by Clopidogrel in vitro," British Journal of Pharmacology, 126, pp. 415-210, 1999.
Wiviott et al., "Prasugrel," Circulation, 122, pp. 394-403, 2010.
Written Submission filed by Daiichi Sankyo for EP 1 350 511 dated Dec. 24, 2010.
Written Submission for EP 1 350 511 dated Jan. 20, 2011.
Written Submission for EP 1 350 511 dated Feb. 18, 2011.
Ziemianin et al., "Thienopyridines: Effects on Cultured Endothelial Cells," Journal of Physiology and Pharmacology, 50(4), pp. 597-604, 1999.

Abou-Khalil et al., "Effects of Ticlopidine, A New Platelet Antiaggregating Agent, and Its Analogues on Mitochondrial Metabolism," Biochemical Pharmacology, 33(23), pp. 3893-3898, 1984.
Abou-Khalil et al., "Mechanism of Interaction of Ticlopidine and Its Analogues With the Energy-Conserving Mechanism in Mitochondria," Biochemical Pharmacology, 35(11), pp. 1855-1859, 1986.
Abou-Khalil et al., "Swelling of Mitochondria by the Platelet Antiaggregating Agent Ticlopidine," Biochemical Pharmacology, 35(11), pp. 1849-1853, 1986.
Antman et al., "ACC/AHA Guidelies for the Management of Patients with Unstable Angina and Non-ST-Segment Elevation Myocardial Infarction," Journal of American College of Cardiology, 36(3), pp. 970-1062, 2000.
Aono et al., "Effects of a New Antihypertensive Agent, SGB-1534, on Rat Platelet Aggregation," Japan J. Pharmacol., 42, pp. 493-500, 1986.
Armstrong et al., "Reduction of Platelet Thromboxane $A_2$ Production ex vivo and in vivo by Clopidogrel Therapy," International Society on Thrombosis and Haemostasis, pp. 613-615, 2009.
Asai et al., "CS-747, a New Platelet ADP Receptor Antagonist," Annu. Rep. Sankyo Res. Lab., 54, pp. 1-44, 1999.
Asai et al., "CS-747 (Prasugrel, LY640315) Produces Potent and Sustained Platelet Inhibitory Effects in Dogs and Monkeys During Multiple Dosing That Are Enhanced by Co-administration of Aspirin," J. Thromb. Haemost., 2005; 3 (Suppl. 1): P1111, Abstract and poster presentation.
Asai et al., "Effects of CS-747, a novel P2Y12 receptor antagonist, on cerebral and peripheral arterial occlusive diseases in rats," J. Thromb. Haemostasis, 2003; 1 (suppl. 1): P2033.
Asai et al., "Flow cytometric analysis of VASP phosphorylation in platelets treated with the active metabolite of prasugrel, a P2Y12 ADP receptor antagonist," J. Thromb. Haemost., 2007; 5 (Suppl. 2): P-S-652, Abstract and poster presentation.
Asai et al., "The P2TAC receptor antagonistic actions of CS-747 and its metabolite, R-99224, in rats," J. Thromb. Haemost., 2001; Abst 1915, Abstract and poster presentation.
Baron et al., "Effects of the Gp IIb/IIIa Antagonist SC-54701 of Fibrin Generation and Platelet-Fibrin Interactions in Thrombin Induced Clot Formation and Retraction," Thromb. Haemostasis, #1593, 73, No. 6, 1315, 1995.
Bassand, "Combination Therapy or Triple-Antiplatelet Therapy?," the Heart.org, retrieved from http://www.theheart.org/documents/sitestructure/en/content/programs/1227579/1227579.ht . . . retrieved on Jul. 22, 2011.
Bassand, "Platelet Antiaggregation Treatment in the Aftermath of GUSTO IV, TARGET, TACTICS, and CURE Trials," Rev. Esp. Cardiol., 55(7), pp. 697-702, 2002.
Berge et al., "Pharmaceutical Salts," Journal of Pharmaceutical Sciences, 66(1), pp. 1-19, Jan. 1977.
Bertrand et al., Double-Blinded Study of the Safety of Clopidogrel With and Without a Loading Dose in Combination with Aspirin compared with Ticlopidine in Combination with Aspirin after Coronary Stenting: The Clopidogrel Aspirin Stent International Cooperative Study (CLASSICS), Circulation 102, pp. 624-629, 2000.
Bhatt, "Intensifying Platelet Inhibition—Navigating Between Scylla and Charybdis," N. Engl. J. Med., 357(20), pp. 2078-2081, Nov. 15, 2007.
Bloom, "Comprehensive Toxicology: Modulation of Platelet Function by Xenobiotics: Toxicologic Implications," (Jakubowski) vol. 4, pp. 247-261, 1997.
Boneu et al., "Platelet Anti-Aggregating Activity and tolerance of clopidogrel in atherosclerotic patients," *Thromb Haemost.*, 76(6), pp. 939-943, Dec. 1996.
Boysen, "Bleeding Complications in Secondary Stroke Prevention by Antiplatelet Therapy: A Benefit-Risk Analysis," Journal of Internal Medicine, 246, pp. 239-245, 1999.
Braunwald et al., ACC/AHA Guidelines for the Management of Patients with Unstable Angina and Non-ST-Segment Elevation Myocardial Infarction: Executive Summary and Recommendations: A Report of the American College of Cardiology/American Heart

(56) References Cited

OTHER PUBLICATIONS

Association Task Force on Practice Guidelines (Committee on the Management of Patients with Unstable Angina), Circulation, 102, pp. 1193-1209, 2000.

Brown et al., "Comparison of Antiplatelet Activity of Microencapsulated Aspirin 162.5 mg (Caspac XL), with Enteric Coated Aspirin 75 mg and 150 mg in Patients with Atherosclerosis," Blackwell Science Ltd. Br. J. Clin. Pharmocol., 48, pp. 57-62, 1999.

Buckland et al., "Prasugrel active metabolite yields complete inhibition of P2Y12-mediated amplification of platelet responses," UK Platelet Meeting 2006.

Buckland et al., "Cangrelor inhibits the binding of clopidogrel and prasugrel active metabolites to the P2Y12 receptor," Congress of the European Society of Cardiology 2009.

Buckland et al., "Reversible binding of cangrelor to the P2Y12 receptor prevents the binding of clopidogrel and prasugrel active metabolites," J. Thromb. Haemost., 2009; 7 (suppl. 2): 589-590.

Budd et al., "The Effectiveness of Low Dose Slow Release Aspirin as an Antiplatelet Agent," Journal of the Royal Society of Medicine, 86, pp. 261-263, May 1993.

Hirsh et al., "Aspirin and Other Platelet-Active Drugs: The Relationship Among Dose, Effectiveness, and Side Effects," Chest, 108, pp. 247S-257S. 1995.

Daiichi Sankyo Company Ltd., and Eli Lilly and Company, "Daiichi Sankyo and Lilly Announce TRILOGY ACS Results Regarding Effient® (Prasugrel) in Acute Coronary Syndrome UA/NSTEMI Patients to be Managed Medically without an Artery-Opening Procedure," Press Release, Aug. 26, 2012, pp. 1-8.

Roe et al., "Prasugrel versus Clopidogrel for Acute Coronary Syndromes without Revascularization," N. Engl. J. Med., pp. 1-13 (Aug. 26, 2012).

TRILOGY ACS Investigators (Duke Clinical Research Institute), "Prasugrel vs. Clopidogrel for Acute Coronary Syndromes Patients Managed without Revascularization—the TRILOGY ACS trial," Presentation from ESC Congress 2012, Munich, Germany (Aug. 26, 2012)(20 pages total).

De Caterina, "TRILOGY ACS: Prasugrel versus clopidodrel for patients with Unstable Angina/NSTEMI who are medically managed without revascularization," Presentation, from ESC Congress 2012, Munich, Germany (Aug. 26, 2012)(9 pages total).

Grounds of Appeal of Daiichi Sankyo Company, Limited & Ube Industries, Ltd. Against the Decision of the Opposition Division to Revoke European Patent No. 1 350 511, dated Oct. 27, 2011, 35 pages.

Submission by Opponent Ratiopharm GmbH dated Mar. 16, 2012 in Response to Patentee's Statement Setting out the Grounds of Appeal dated Oct. 27, 2011 for EP 1 350 511, 19 pages.

Makkar et al., "Clopidogrel is More Effective Than Aspirin in Inhibiting Acute Stent Thrombosis," Journal of the American College of Cardiology, Abstract No. 991-45, vol. 27, No. 2, pp. 333A-334A, Feb. 1996.

Campo et al., "Poor Responsiveness to Clopidogrel: Drug-Specific or Class-Effect Mechanism," Journal of American College of Cardiology, 50(12), pp. 1132-1137, 2007.

CAP Today, "GRAVITAS Findings Part of Plavix Puzzle," College of American Pathologists, retrieved from http://www.cap.org/apps/cap.portal?nfpb=true&cntvwrPtltactionOverride=%2Fportlets%2 FcontentViewer%2Fshow&windowLabel=cntvwrPtit&cntvwr Ptit%7BactionForm.contentReference%7D=captoday%2 F1210%2F1210cplavix.html&state=.maximized&pageLabel= cntvwr, Dec. 2010.

Cattaneo et al., "ADP Receptors and Clinical Bleeding Disorders," Arterioscler Thromb Vasc Biol., 19, pp. 2281-2285, 1999.

Chhaya J. Shah, Pharm. D., Curriculum Vitae, May 2006.

Clarke et al., "Suppression of Thromboxane $A_2$ But Not of Systemic Prostacyclin by Controlled-Release Aspirin," The New England J. of Medicine, 325(16), pp. 1137-1141, 1991.

Crofts et al., "Functional Significance of Different Human CYP1A1 Genotypes," Carcinogenesis, 15(12), pp. 2961-2963, 1994, Abstract only.

Currie et al., "Enhanced Circulatory Parameters of Human Platelets Cryopreserved with Second-Messenger Effectors: an in vivo Study of 16 Volunteer Platelet Donors," British Journal of Haematology, 105, pp. 826-831, 1999.

Daiichi Sankyo Company Ltd, "Further Observations of the Proprietors in Relation to the Defence of EP 1 350 511 Against Oppositions, and in Preparation for Oral Proceedings, Mar. 22, 2011," dated Dec. 24, 2010.

DeRay et al., "Clopidogrel Activities in Patients with Renal Function Impairment," Clinical Drug Investigation, 16(4), pp. 319-328, Oct. 1, 1998, Abstract only.

Diener et al., "European Stroke Prevention Study 2. Dipyridamole and Acetylsalicyclic Acid in the Secondary Prevention of Stroke," J. of the Neurological Sciences, 143, pp. 1-13, 1996.

Dobesh, "Clopidogrel Versus Prasugrel: Times are Changing, but Not for Everyone," Pharmacotherapy, 29(12), pp. 1393-1396, 2009.

Dovlatova et al., "Competition between reversible and irreversible P2Y12 antagonists and its influence on ADP-mediated platelet activation," J. Thromb. Haemost., 2007; 5 (Suppl. 2): P-S-340.

The Epic Investigators, "Use of a Monoclonal Antibody Directed Against the Platelet Glycoprotein IIb/IIIa Receptor in High-Risk Coronary Angioplasty," The New England Journal of Medicine, 330(14) pp. 956-961, Apr. 7, 1994.

Ernest et al., "Population Pharmacokinetics and Pharmacodynamics of Prasugrel and Clopidogrel in Aspirin-Treated Patients with Stable Coronary Disease," J. Pharmacokinet Pharmacodyn, 35, pp. 593-618, 2008.

Esato et al., "Satigrel, a New Antiplatelet Agent, Inhibits Platelet Accumulation in Prosthetic Arterial Grafts," Am. J. Surg., 175, pp. 56-60, 1998.

European Patent No. 1350511 in the name of Daiichi Sankyo Company, Limited, Decision Revoking the European Patent, dated Jun. 17, 2011.

European Patent No. 1350511 in the name of Daiichi Sankyo Company, Limited, Provision of a copy of the minutes in accordance with Rule 124(4) EPC, dated Jun. 17, 2011.

European Opposition by Ratiopharm GmbH filed Jun. 19, 2009 against European Patent No. 1 350 511, which issued from European Application No. 01271850.8.

Ferguson et al., "Antiplatelet Therapy in Clinical Practice," Martin Duntiz, Chapters 6 and 8-11, 2000.

Figure 2, Food and Drug Administration (FDA) Approval Document for Plavix (Generic Name, Clopidogrel Bisulphate), approved Nov. 17, 1997.

Frelinger III, et al., "The active metabolite of prasugrel (CS-747) inhibits ADP-stimulated thrombo-inflammatory markers of platelet activation: Leukocyte-platelet and platelet-platelet aggregation and platelet surface P-selectin and activated GPIIb-IIIa," Circulation, 2005; 112(17), Supp. [2]: U449-U449. MA 1904.

Frelinger III, et al., "The active metabolite of prasugrel (CS-747) inhibits ADP-stimulated thrombo-inflammatory markers of platelet activation: Modulation by other blood cells and calcium, but not by aspirin," J. Am. Coll. Cardiol., 2006; 47(4), Supp. [A]: 364A-364A.

Giezen, "Optimizing Platelet Inhibition," European Heart Journal Supplements, 10(D), pp. D23-D29, 2008.

Glasson et al., "Multiple Human Serum Binding of Two Thienopyridinic Derivatives, Ticlopidine and PCR 2362, and Their Distribution Between HAS, $\alpha_1$-Acid Glycoprotein and Lipoproteins," Biochemical Pharmacology, 31(5), pp. 831-835, 1982.

Gorelick et al., "Therapeutic Benefit: Aspirin Revisited in Light of the Introduction of Clopidogrel," Stroke, 30, pp. 1716-1721, 1999.

Gotoh et al., "Cilostazol Stroke Prevention Study: A Placebo-Controlled Double-Blind Trial for Secondary Prevention of Cerebral Infarction," J. of Stroke and Cerebrovascular Diseases, 9(4), pp. 147-157, 2000.

Grossmann et al., "Variable Extent of Clopidogrel Responsiveness in Patients After Coronary Stenting," Thromb. Haemost, 92, pp. 1201-1206, 2004.

Gurbel et al., "Clopidogrel for Coronary Stenting. Response Variability, Drug Resistance, and the Effect of Pretreatment Platelet Reactivity," Circulation, 107, pp. 2908-2913, 2003.

(56) References Cited

OTHER PUBLICATIONS

Gurbel et al., "Combination Antithrombotic Therapies," Circulation, 121, pp. 569-583, 2010.
Hankey et al., "Thienopyridines or Aspirin to Prevent Stroke and Other Serious Vascular Events in Patients at High Risk of Vascular Disease?: A Systematic Review of the Evidence from Randomized Trials," Stroke, 31, pp. 1779-1784, 2000.
Herbert et al., "Biochemical and Pharmacological Activities of SR 26831, A Potent and Selective Elastase Inhibitor," The Journal of Pharmacology and Experimental Therapeutics, 260(2), pp. 809-816, 1992.
Holmes et al., "ACCF/AHA Clopidogrel Clinical Alert: Approaches to the FDS Boxed Warning, " Circulation, 122, pp. 537-557, 2010.
Huang et al., "Prevention of Arterial Thrombosis by Intravenously Administered Platelet P2T Receptor Antagonist AR-C69931 MX in a Canine Model," The Journal of Pharmacology and Experimental Therapeutics, 295(2), pp. 492-499, 2000.
Ikeda et al., "Pharmacokinetics and Disposition of CD-747, a New Pro-drug ADP-Receptor Antagonist, in Rats and Dogs," Thromb. Haemost., 82, 1999, p. 829, Abstr. 2627.
Iida et al. "A Potent and Specific Non-Peptide GPllb/llla Antagonist," Thromb.Haemostasis, #1595, 73, No. 6, 1315, 1995.
Jakubowski, J.A. et al., "A comparative study of the effects of prasugrel (CS-747, LY640315) and clopidogrel on platelet function in healthy subjects," Am. J. Cardiol., 2005; 96(7A): 149.
Jakubowski, J.A. et al., "Comparison of a novel Elisa-based VASP whole blood (WB) assay with the flow cytometric (FC) technique," J. Thromb. Haemost., 2009; 7 (suppl. 2): 942.
Jakubowski, J.A. et al., "Comparative Antiplatelet Effects of the Active Metabolites of CS-747 (Prasugrel, LY640315) and Clopidogrel," J. Thromb. Haemost., 2005; 3 (Suppl. 1): P2299.
Jakubowski, J.A. et al., "Platelet inhibitory effects of R-138727, the active metabolite of CS-747 a potent thienopyridyl P2Y-12 antagonist prodrug," FASEB J., 2002; 16, No. 4, Pt. 1, A203.
Jakubowski et al., "Prasugrel: A Novel Thienopyridine Antiplatelet Agent. A Review of Preclinical Studies and the Mechanistic Basis for Its Distinct Antiplatelet Profile," Cardiovascular Drug Reviews, 25(4), pp. 357-374, 2007.
Jakubowski et al., "Preclinical Efficacy of Prasugrel (CS-747, LY640315), a Novel and Potent Thienopyridine Oral P2Y12 ADP Receptor Antagonist," World Atherosclerosis Summit 2005.
Jakubowski et al., "Stereoselective inhibition of human platelet aggregation by active metabolite of CS-747, a novel P2Y12 receptor antagonist," J. Thromb. Haemostasis, 2003; 1 (suppl. 1): P2056.
Judge et al., "P2Y12 blockade by prasugrel active metabolite yields complete inhibition of P2Y12-mediated amplification of platelet responses," J. Thromb. Haemost., 2007; 5 (Suppl. 2): P-M-343.
Judge et al., "Platelet function assays that assess response to P2Y12 antagonists vary widely in their sensitivities to low levels of P2Y12 receptor blockade," Eur. Heart J., 2008; 29 (Abstract Supplement): 835.
Judge et al., "The Active Metabolite of Prasugrel Effectively Blocks the Platelet $P2Y_{12}$ Receptor and Inhibits Procoagulant and pro-inflammatory Platelet Responses," Platelets, 19(2), pp. 125-133, Mar. 2008.
Katano et al., "Tetrahydrothienopyridine Derivatives as Novel GPIIB/IIIA Antagonists," Bioorganic & Medicinal Chemistry Letters, 6(21), pp. 2601-2606, 1996.
Kawano et al., "ME3277, a GPllb/llla Antagonist Reduces Cerebral Infarction Without Enhancing Intracranial Hemorrhage in Photothrombotic Occlusion of Rabbit Middle Cerebral Artery," Journal of Cerebral Blood Flow and Metabolism, 20, pp. 988-997, 2000.
Kawano et al., "Superiority of Platelet Integrin GPllb-llla Receptor Antagonist over Aspirin in Preventing Cyclic Flow Reductions in the Guinea Pig Middle Cerebral Artery," European Journal of Pharmacology, 374, pp. 377-385, 1999.
Kishi et al., "Ibudilast Modulates Platelet-Endothelium Interaction Mainly Through Cyclic GMP-Dependent Mechanism," Journal of Cardiovascular Pharmacology, 36(1), pp. 65-70, Jul. 2000.
Kristensen, "Antithrombotic Treatment in Patients with Type 2 DM," Slide presentation, Copenhagen, Denmark 190710, WorldPharma Jul. 17-23, 2010.
Krupinski et al., "The Antithrombotic Effect of Thromboxane Receptor Antagonist HN 11500 on Thrombus Formation in Laser Thrombosis Model and Platelet Function Tests," Acta Haematol. Pol., 25(3), pp. 235-242, 1994, Abstract only.
Kurihara et al., "Potent inhibition of platelet aggregation by prasugrel (CS-747, LY640315), a novel thienopyridine antiplatelet agent, is associated with covalent binding of active metabolite to ADP receptor," Eur. Heart J., 2005; 26, No. Suppl. 1: 485, Abstract and poster.
Lazar et al., "Prasugrel for Acute Coronary Syndromes: Faster, More Potent, but Higher Bleeding Risk," Cleveland Clinic Journal of Medicine, 76(12), pp. 707-713, Dec. 2009.
Leadbeater et al., "In vitro Aspirin Has Little Additional Anti-Platelet Effect in the Presence of Prasugrel Active Metabolite," Proceedings of the British Pharmacological Society at http://mvw.pA2online.org/abstracts/vol8issue/abst146P.pdf, Dec. 15, 2010, Abstract only.
Lenz et al., "Aggrenox: A Fixed-Dose Combination of Aspirin and Dipyridamole," The Annals of Pharmacotherapy, 34, pp. 1283-1290, 2000.
Maruyama et al., "A Randomized Trial of E5510 Versus Aspirin in Patients with Transient Ischemic Attacks: The Japanese E5510 TIA Study-1 (JETS-1) Group," Angiology, 46(11), 999-1008, 1995.
Meng et al., "Effect of Acetylsalicyclic Acid on Experimentally Induced Arterial Thrombosis in Rats," Naunyn-Schmiedeberg's Arch. Pharmacol., 301, pp. 115-119, 1977.
Mehta et al., "Effects of Pretreatment with Clopidogrel and Aspirin Followed by Long-Term Therapy in Patients Undergoing Percutaneous Coronary Intervention: the PCI-CURE Study," the Lancet, 358, pp. 527-533, Aug. 18, 2001.
Meiji Seika: Activities Abroad Extended, Bulletin International Abstract, Paris, France, Feb. 1997.
Milani et al., "Effects of Picotamide, an Antiplatelet Agent, on Cardiovascular Events in 438 Claudicant Patients with Diabetes: a Retrospective Analysis of the ADEP Study," Br. J. Clin. Pharmacol., 42, pp. 782-785, 1996.
Morikawa et al., "Sex Difference in the Effect of Aspirin on Rat Platelet Aggregation and Arachidonic Acid Metabolism," Japan J. Pharmacol., 37, pp. 317-323, 1985.
Mousa et al., "Comparative in vitro Efficacy of Different Platelet Glycoprotein llb/llla Antagonists on Platelet-Mediated Clot Strength Induced by Tissue Factor with Use of Thromboelastography: Differentiation Among Glycoprotein llb/llla Antagonists," Arterioscler Thromb Vasc Biol., 20, pp. 1162-1167, 2000.
Nagle, "Mixed Results Dampen Expectations for Eli Lilly's Prasugrel," retrieved from www.outsourcin-pharma.com/content/view/print/325169, Nov. 5, 2007.
Nainggolan et al., "Ticagrelor Approval: US and Europe React," retrieved from http://www.theheart.org/article/1255711/print.do, Jul. 21, 2011.
Narita et al., "Antithrombotic Effect of TA-993, a Novel 1,5-Benzothiazepine Derivative, in Conscious Rats," Jpn. J. Pharmacol., 68, pp. 397-404, 1995.
Niitsu et al., "CS-747 (Prasugrel, LY640315), A Novel Antiplatelet Agent, Inhibits Arterial Thrombosis Through Selective Blockade of Platelet P2Y12 Receptors," J. Thromb. Haemost., 2005; 3 (Suppl. 1): P1708.
Norgard, et al., "Comparison of Prasugrel and Clopidogrel in Patients with Acute Coronary Syndrome Undergoing Percutaneous Coronary Intervention," Vascular Health and Risk Management, 5, pp. 873-882, 2009.
O'Conor et al., "$5-HT_{1b}$ And $5-HT_{2A}$ Receptor Antagonist Properties of SL 65.0472 *in vivo*," Br. J. Pharmacol., 129, Proc., 58P, 2000.
Office Action dated Oct. 15, 2010 in U.S. Appl. No. 11/520,168.
Ogawa et al., "Direct evidence for binding of the active metabolite of prasugrel (CS-747, LY640315), a novel thienopyridine antiplatelet drug, to human platelets," Eur. Heart J., 2006; 27, Suppl. 1, Abs. P4550.
Ogawa et al., "Comparison of Antiplatelet and Antithrombotic Effects of Prasugrel and AZD6140," J. Thromb. Haemost., 2007; 5 (Suppl. 2): P-T-645.

(56) References Cited

OTHER PUBLICATIONS

Ogawa et al., "Effective Inhibition of Platelet Aggregation and Release Reaction With Lack of Effect on Shape Change by CS-747 (Prasugrel, LY640315) And Its Active Metabolite," J. Thromb. Haemost., 2005; 3 (Suppl. 1): P2301.

Ogawa et al., "Effects of Prasugrel, a Novel $P2Y_{12}$ Inhibitor, in Rat Models of Cerebral and Peripheral Atery Occulive Disease," European Journal of Pharmacology, 612, pp. 29-34, 2009.

Okudaira et al., "A Study of the Intestinal Absorption of an Ester-Type Prodrug ME3229, in Rats: Active Efflux Transport as a Cause of Poor Bioavailability of the Active Drug," The Journal of Pharmacology and Experimental Therapeutics, 294(2), pp. 580-587, 2000.

Okudaira et al., "Polarized Efflux of Mono- and Diacid Metabolites of ME3229, an Ester-Type Prodrug of a Glyoprotein llb/llla Receptor Antagonist, in Rat Small Intestine," The Journal of Pharmacology and Experimental Therapeutics, 295(2), pp. 717-723, 2000.

O'Riordan, "FDA Advisory Panel Votes Unanimously in Favor of Prasugrel," retrieved from http://www.theheart.org/article/939227.do, Heartwire, Feb. 4, 2009.

O'Riordan, "Prasugrel Bests Clopidogrel Without Bleeding Risk in STEMI Subgroup in TRITON-TIMI 38, Researchers Say," retrieved from http://www.theheart.org/articie/944803/print.do, Mar. 5, 2009.

Otsuguro et al., "Antiplatelet, antithrombotic and antihemostatic effects of multiple administration of CS-747, a novel P2TAC receptor antagonist, in rats," J. Thromb. Haemost., 2001; Abst 1901.

Plavix® —Committee for Proprietary Medicinal Products European Public Assessment Report (EPAR), The European Agency for the Evaluation of Medicinal Products, revision 2, Oct. 2000.

Poster Presentations, "Mechanisms of Platelet Activation I," The Authors. Journal Compilation, International Society on Thrombosis and Hemostasis, 7(2), 1-1204, poster presentations 317, 572, and 573, 2009.

Preliminary Opinion of the Opposition Division and Summons to Attend Oral Proceedings Pursuant to Rule 115(1) EPC dated Oct. 7, 2010 for European Patent Application No. 01271850.8.

The RAPT Investigators, "Randomized Trial of Ridogrel, A Combined Thromboxane $A_2$ Synthase Inhibitor and Thromboxane $A_2$/Prostaglandin Endoperoxide Receptor Antagonist, Versus Aspirin as Adjunct to Thrombolysis in patients with Acute Myocardial Infarction," Circulation, 89, pp. 588-595, 1994.

Rauch et al., "Mitogenic and Proinflammatory Actions of Thrombin-regulated P2Y12 ADP Receptor in Human Vascular Smooth Muscle Cells," Circulation, 2010; 23: 122: A15821.

Rauch et al., "Thrombin upregulated expression of functionally active P2Y(12) ADP receptors in human vascular smooth muscle cells," $50^{th}$ Annual Meeting, Deutsche Gesellschaft fur Experimentelle und Klinische Pharmakologie und Toxikologie, Mainz, Mar. 10-12, 2009, Naunyn-Schmiedeberg's Arch Pharmacol., 379 (suppl. 1), Abstract 484 (p. 96), pp. 1-100, 2009.

Rechner et al., "The sensitivity of a new cartridge for the PFA-100® system to inhibition of platelet function by the active metabolite of prasugrel (R-138727)," Gesellschaft fur Thrombose- und Hamostaseforschung 2008 Congress Feb. (2008).

Satoh et al., "GP llb-llla Antagonists Like Lamifiban (Ro 44/9883) That do not Induce Conformational Changes are Potent Inhibitors of Platelet Adhesion to Fibrinogen," Thromb.Haemostasis #1594, 73, No. 6, 1315, 1995.

Serebruany et al., "Combination Antiplatelet Therapy with Aspirin and Clopidogrel: The Role of Antecedent and Concomitant Doses of Aspirin," Cardiology, 107, pp. 307-312, 2007.

Serebruany et al., "Platelet Inhibition with Prasugrel (CS-747) Compared with Clopidogrel in Patients Undergoing Coronary Stenting: the Subset from the JUMBO Study," Postgrad Med J, 82 pp. 404-410, 2006, Abstract only.

Shuldiner et al., "Association of Cytochrome P450 2C19 Genotype with the Antiplatelet Effect and Clinical Efficacy of Clopidogrel Therapy," JAMA, 302(8), pp. 849-858, Aug. 26, 2009.

Siegbahn et al., "Greater Platelet P2Y12 Inhibition by Prasugrel Compared to High Dose Clopidogrel Assessed by VASP Phosphorylation in Patients with Stable Coronary Artery Disease," J. Thromb. Haemost., 2007; 5 (Suppl. 2): O-T-031.

Slugg et al., "Cirrhosis Does Not Affect the Pharmacokinetics and Pharmacodynamics of Clopidogrel," The Journal of Clinical Pharmacology, 40, pp. 396-401, 2000.

Smith et al., "ACC/AHA Guideline for Percutaneous Coronary Intervention (Revision of the 1993 PTCA Guideline)-Executive Summary: A report of the American College of Cardiology/American Heart Association Task Force on Practice Guidelines (Committee to the Revise the 1993 Guidelines for Percutaneous Transluminal Coronary Angioplasty Endorsed by the Society for Cardiac Angiography and Interventions," Circulation, 103, pp. 3019-3041, 2001.

Smith et al., "AHA/ACC Guidelines for Preventing Heart Attack and Death in Patients with Atherosclerotic Cardiovascular Disease: 2001 Update: A Statement for Healthcare Professional from the American Heart Association and the American College of Cardiology," J. Am. Coll. Cardiol., 38, pp. 1581-1583, 2001.

First Declaration of Professor Stanley Heptinstall in the matter of European Patent No. Ep 1350511, in the name of Daiichi Sankyo Company et al., and Opposed by Helm AG, and Ratiopharm GmbH, Oct. 25, 2011.

Second Declaration of Professor Stanley Heptinstall in the matter of European Patent No. Ep 1350511, in the name of Daiichi Sankyo Company, Limited and Ube Industries, Ltd. And Oppositions thereto by Helm AG, Teva Pharmaceutical Industries, Ltd. And Ratiopharm GmbH, Oct. 26, 2011.

Steinhubl et al., "Point-of-Care Measured Platelet Inhibition Correlates With a Reduced Risk of an Adverse Cardiac Event After Percutaneous Coronary Intervention," Circulation, 103, pp. 2572-2578, 2001.

Storey et al., "First Clinical Study of the Novel Platelet ADP Receptor ($P_{2T}$) Antagonist AR-C69931MX, Assessing Safety, Tolerability and Activity in Patients With Acute Coronary Syndromes," Circulation, Abstract #3745, 1999.

The Stroke Prevention in Reversible Ischemia Trial (SPIRIT) Study Group, "A Randomized Trial of Anticoagulants Versus Aspirin After Cerebal Ischemia of Presumed Arterial Origin," Ann. Neurol., 42, pp. 857-865, 1997.

Sugidachi et al., "Active Metabolites of CS-747 (Prasugrel, LY640315) and Clopidogrel Show Similar in Vitro P2Y12 Receptor Blockade But Greater In Vivo Potency of CS-747," J. Thromb. Haemost., 2005; 3 (Suppl. 1): P1109.

Sugidachi et al., "Effects of prasugrel (CS-747, LY640315) on platelet aggregation in P2Y12 receptor-deficient mice: Evidence for specific inhibition of P2Y12 receptors by prasugrel," Eur. Heart J., 2006; 27, Suppl. 1, Abs. P4557.

Sugidachi et al., "Influence of Thienopyridines on Atherosclerotic Lesion Induced by Cholesterol Feeding in Two Animal Models," Circulation, 2008; 118(18), Suppl. 2: S478.

Sugidachi et al., "The effects of major in vivo metabolites of prasugrel on human platelet aggregation," J. Thromb. Haemost., 2009; 7 (suppl. 2): 349.

Swanson et al., "Effect of BMS-18029, A long Acting Thromboxane A2 Receptor Antagonist, on Platelet Function in Healthy Men," Clinical Pharmacology & Therapeutics, 202, Plll-82, Feb. 1994.

Szalony et al., "Extended Inhibition of Platelet Aggregation with the Orally Active Platelet Inhibitor SC-54684A," Circulation, 91, pp. 411-416, 1995.

Takai et al., "Hydolytic Profile for Ester-or Amide-linkage by Carboxylesterases pI 5.3 and 4.5 from Human Liver," Biol. Pharm. Bull., 20(8), pp. 869-873, 1997.

Testa et al., "Current Concepts on Antiplatelet Therapy, Focus on the Novel Thienopyridine and Non-Thienopyridine Agents," Hindawi Publishing Corporation, Advances in Hematology, Article ID 595934, 2010.

Todoruk, "Eli Lilly, Daiichi Sankyo's Effient Garners FDA Approval," FirstWord™, retrieved from www.firstwordplus.com, Jul. 10, 2009.

Tourmousoglou et al., "Clopidogrel and aspirin in cardiovascular medicine: responders or not—current best available evidence," Cardiovasc Hematol Agents Med Chem., 6(4), pp. 312-322, Oct. 2008.

(56) References Cited

OTHER PUBLICATIONS

"Thrombosis Prevention Trial: Randomised Trial of Low-Intensity Oral Anticoagulation with Warfarin and Low-Dose Aspirin in the Primary Prevention of Ischaemic Heart Disease in Men at Increased Risk. The Medical Research Council's General Practice Research Framework," Lancet, 351, pp. 233-241, Jan. 24, 1998, Abstract only.

Varenhorst et al., "Assessment of the platelet inhibitory effect of clopidogrel and prasugrel by the VerifyNow™ P2Y12 point-of-care device in comparison with LTA and VASP-phosphorylation in patients with stable coronary artery disease," Eur. Heart J., 2008; 29 (Abstract Supplement): 404.

Varenhorst et al., "Genetic Variation of CYP2C19 Affects Both Pharmacokinetic and Pharmacodynamic Responses to Clopidogrel but Not Prasugrel in Aspirin-Treated Patients with Coronary Artery Disease," Circulation, Jul. 8, 2008.

Venkatesan, "Why Prasugrel is heavily Indebted to Aspirin for its Glory? . . . The Curious Case of Human Platelet Business," Expressions in Cardiology, retrieved from http://drsvenkatesan.worldpress.com/2011/02/28/why-prasugrel-is heavil...to-aspirin-for-its-glory-the-curious-case-of-human-platelet-business/, Feb. 28, 2011.

Verstraete et al., Cardiovascular Thrombosis. Thrombocardiology and Thromboneurology, Second Edition, Lippincott-Raven Publishing, Chapters 9-11, 14 and 17, 1998.

Vetrano et al., "Effects of Aspirin or Picotamide, an Antithromboxane Agent, in Combination with Low-Intensity Oral Anticoagulation in Patients with Acute Myocardial Infarction: a Controlled Randomized Pilot Trial," G. Ital. Cardiol., 29(5), pp. 524-528, May 1999, Abstract only.

Vlachojannis et al., "Clopidrogel Resistance: Current Aspects and Future Directions," Hellenic J. Cardiol., 52, pp. 236-245, 2011.

Wada, et al., "Correlation of Inhibition of Platelet Aggregation with Cardiovascular and Bleeding Outcomes in Acute Coronary Syndromes," The Journal of Clinical Pharmacology, 50(8), pp. 904-913, Aug. 2010, Abstract only.

Weksler, "Antiplatelet Agents in Stroke Prevention. Combination Therapy: Present and Future," Cerebrovasc. Dis., 10, suppl. 5, pp. 41-48, 2000, abstract only, retrieved from www.ncbi.nlm.nih.gov/pubmed/11096182.

Younossi et al., "Effect of Combined Anticoagulation and Low-Does Aspirin Treatment on Upper Gastrointestinal Bleeding," Digestive Diseases and Sciences, 42(1), pp. 79-82, Jan. 1997.

METHOD OF TREATMENT WITH COADMINISTRATION OF ASPIRIN AND PRASUGREL

This is a Divisional Application of application U.S. Ser. No. 10/600,266 filed Jun. 20, 2003, pending, which is a Continuation Application of International Application No. PCT/JP01/11201 filed Dec. 20, 2001, which is incorporated herein by reference in its entirety.

BACKGROUND OF THE INVENTION

This invention relates to pharmaceutical compositions containing 2-acetoxy-5-(α-cyclopropylcarbonyl-2-fluorobenzyl)-4,5,6,7-tetrahydrothieno[3,2-c]pyridine (Prasugrel) or a pharmaceutically acceptable salt thereof, and aspirin, as active ingredients [particularly pharmaceutical compositions for prevention or treatment (particularly for treatment) of diseases caused by thrombus or embolus]; to the use of 2-acetoxy-5-(α-cyclopropylcarbonyl-2-fluorobenzyl)-4,5,6,7-tetrahydrothieno[3,2-c]pyridine or a pharmaceutically acceptable salt thereof and aspirin for the manufacture of pharmaceutical compositions for prevention or treatment (particularly for treatment) of diseases caused by thrombus or embolus; and to methods for the prevention or treatment (particularly to methods for the treatment) of diseases caused by thrombus or embolus by administration of an effective amount of 2-acetoxy-5-(α-cyclopropylcarbonyl-2-fluorobenzyl)-4,5,6,7-tetrahydrothieno[3,2-c]pyridine or a pharmaceutically acceptable salt thereof and aspirin to warm-blooded animals (particularly humans).

2-Acetoxy-5-(α-cyclopropylcarbonyl-2-fluorobenzyl)-4,5,6,7-tetrahydrothieno[3,2-c]pyridine has been described in the Japanese Patent Application Publication No. Hei 6-41139, and possesses potent inhibitory activity against platelet aggregation. Furthermore, aspirin is well known to have an inhibiting activity against platelet aggregation, although the activity is low. However, pharmaceutical compositions containing both compounds have not been known.

BRIEF DESCRIPTION OF THE INVENTION

The present inventors have studied therapeutic agents with low toxicity that exert inhibitory activity against platelet aggregation and have found that the problems described above are solved by using pharmaceutical compositions comprising 2-acetoxy-5-(α-cyclopropylcarbonyl-2-fluorobenzyl)-4,5,6,7-tetrahydrothieno[3,2-c]pyridine or a pharmaceutically acceptable salt thereof and aspirin.

DETAILED DESCRIPTION OF THE INVENTION

The present invention provides pharmaceutical compositions containing 2-acetoxy-5-(α-cyclopropylcarbonyl-2-fluorobenzyl)-4,5,6,7-tetrahydrothieno[3,2-c]pyridine or a pharmaceutically acceptable salt thereof and aspirin as active ingredients [particularly pharmaceutical compositions for prevention or treatment (particularly for treatment) of diseases caused by thrombus or embolus]; the use of 2-acetoxy-5-(α-cyclopropylcarbonyl-2-fluorobenzyl)-4,5,6,7-tetrahydrothieno[3,2-c]pyridine or a pharmaceutically acceptable salt thereof, and aspirin, for the manufacture of pharmaceutical compositions [particularly pharmaceutical compositions for prevention or treatment (particularly for treatment) of diseases caused by thrombus or embolus]; and methods for the prevention or treatment (particularly methods for treatment) of diseases caused by thrombus or embolus by administration of an effective amount of 2-acetoxy-5-(α-cyclopropylcarbonyl-2-fluorobenzyl)-4,5,6,7-tetrahydrothieno[3,2-c]pyridine or a pharmaceutically acceptable salt thereof, and aspirin, to warm-blooded animals (particularly humans), simultaneously or sequentially.

2-Acetoxy-5-(α-cyclopropylcarbonyl-2-fluorobenzyl)-4,5,6,7-tetrahydrothieno[3,2-c]pyridine, and pharmaceutically acceptable salts thereof, which is one of the active ingredients of the present invention, is a known compound. For instance, the compound has already been described in Japanese Patent Application Publication No. Hei 6-41139 and Japanese Patent Application Publication No. 2002-145882 (priority: Japanese Patent Application No. 2000-205539, and Japanese Patent Application No. 2000-266780). The chemical structure is described below.

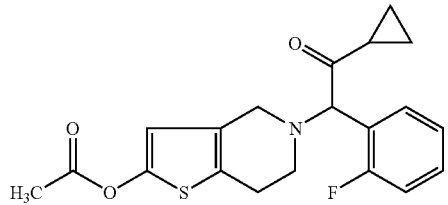 [SMILES: CC(=O)Oc1cc2c(s1)CCN(C(C(=O)C1CC1)c1ccccc1F)C2]

The pharmaceutically acceptable salts of 2-acetoxy-5-(α-cyclopropylcarbonyl-2-fluorobenzyl)-4,5,6,7-tetrahydrothieno[3,2-c]pyridine may be, for example, hydrohalogenic acid salts such as hydrofluoride, hydrochloride, hydrobromide or hydroiodide; nitrate; perchlorate; sulfate; phosphate; $C_1$-$C_4$ alkanesulfonates optionally substituted by halogens such as methanesulfonate, trifluoromethanesulfonate, ethanesulfonate; $C_6$-$C_{10}$ arylsulfonates optionally substituted by $C_1$-$C_4$ alkyl groups such as benzenesulfonate or p-toluenesulfonate; $C_1$-$C_6$ aliphatic acid salts such as acetate, malate, fumarate, succinate, citrate, tartarate, oxalate or maleate; amino acid salts such as glycine salt, lysine salt, arginine salt, ornitine salt, glutamic acid salt or aspartic acid salt; and the preferred compounds are hydrohalogenates or $C_1$-$C_6$ aliphatic acid salts; and more preferred compounds are the hydrochloride or the maleate.

When one of the active ingredients of the present invention, 2-acetoxy-5-(α-cyclopropylcarbonyl-2-fluorobenzyl)-4,5,6,7-tetrahydrothieno[3,2-c]pyridine or a pharmaceutically acceptable salt thereof, is allowed to stand so that it is open to the atmosphere, it may become hydrated by absorption of water or adsorption of water. Such hydrated compounds are included in the present invention.

Further, one of the active ingredients of the present invention, 2-acetoxy-5-(α-cyclopropylcarbonyl-2-fluorobenzyl)-4,5,6,7-tetrahydrothieno[3,2-c]pyridine or a pharmaceutically acceptable salt thereof, may absorb some kinds of organic solvents and may form solvates in some cases, and these solvates are also included in the present invention.

Furthermore, since 2-acetoxy-5-(α-cyclopropylcarbonyl-2-fluorobenzyl)-4,5,6,7-tetrahydrothieno[3,2-c]pyridine has an asymmetric carbon atom, optical isomers exist based on the asymmetric carbon atom. These optical isomers are also included in the present invention.

The other active ingredient, aspirin, is a well-known compound, as an analgesic antipyretic.

The pharmaceutical compositions of the present invention (particularly pharmaceutical compositions for the prevention or treatment of diseases caused by thrombus or embolus) which contain 2-acetoxy-5-(α-cyclopropylcarbonyl-2-fluorobenzyl)-4,5,6,7-tetrahydrothieno[3,2-c]pyridine or a pharmaceutically acceptable salt thereof, and aspirin, as active ingredients, possess excellent inhibitory activity against platelet aggregation and thrombogenesis with short onset latency and low toxicity. Thus the pharmaceutical compositions of the present invention are useful as preventative or therapeutic agents (particularly as therapeutic agents) against diseases caused by thrombus or embolus, for example, diseases induced by platelet aggregation, including stable or unstable angina pectoris and so forth; cardiovascular or cerebrovascular disorders, e.g., thromboembolism, associated with atherosclerosis or diabetes mellitus, such as unstable angina pectoris, cerebral ischemic insult or restenosis due to angioplasty, endarterectomy or stent therapy; or thromboembolism caused by thromboembolization such as recurrent embolism after degradation of the original thrombus, embolism, ischemia-induced dementia, peripheral arteriopathy, thromboembolization associated with hemodialysis or atrial fibrillation, or thromboembolization in the vascular prosthesis, or in the bypass between the aorta and the coronary artery. Furthermore, the therapeutic agent of the present invention is administered to warm-blooded animals (particularly humans).

According to the present invention, the use in combination of 2-acetoxy-5-(α-cyclopropylcarbonyl-2-fluorobenzyl)-4,5,6,7-tetrahydrothieno[3,2-c]pyridine or a pharmaceutically acceptable salt thereof, and aspirin, results in more potent effectiveness than the use of each component alone. Furthermore, plasma levels of these agents do not have to be maintained at a certain level and higher during the same period, in order to produce their effects. It is believed that these 2 agents reach the receptors, at which they act in vivo, and turn on switches at the receptors to induce the effects. Even though the plasma level of one component of the pharmaceutical composition is too low to induce the effects with increasing time after the agent was administered, the switches at the receptors have already been turned on. Thus the preventative or therapeutic efficacy of the agent is expected by inhibiting thrombogenesis or embolization.

Therefore, when the other component of the pharmaceutical composition is administered later, the therapeutic effect of the compound administered later is expected to add to the therapeutic effects of the previously administered component. However, it is convenient clinically that both components are administered at the same time. Thus 2-acetoxy-5-(α-cyclopropylcarbonyl-2-fluorobenzyl)-4,5,6,7-tetrahydrothieno[3,2-c]pyridine or a pharmaceutically acceptable salt thereof and aspirin are simultaneously administered as a combination drug. In the case that both agents cannot be mixed technically, each component can be administered separately. Moreover, as described previously, since each component produces significant effects as a single form, each component can be sequentially administered at appropriate intervals. The maximum intervals between administration of each of the two components that can be accepted to elicit significant effects could be confirmed by clinical trials or animal studies.

The route for administration of 2-acetoxy-5-(α-cyclopropylcarbonyl-2-fluorobenzyl)-4,5,6,7-tetrahydrothieno[3,2-c]pyridine or a pharmaceutically acceptable salt thereof, and aspirin, which is employed in the present invention, is generally the oral route. However, other routes, for example, intravenous administration, can be used. Thus, the 2 components can be prepared respectively as separate formulations, or can be mixed physically to form a single formulation for administration. The single formulations of the mixed components are, for example, powders, granules, tablets, capsules and so forth, and can be prepared by regular formulation techniques, as described below.

These formulations are prepared by conventional methods by using excipients (organic excipients, for example, sugar derivatives such as lactose, sucrose, glucose, mannitol or sorbitol; starch derivatives such as corn starch, potato starch, α-starch or dextrin; cellulose derivatives such as crystalline cellulose; gum arabic; dextran; or pullulan; and inorganic excipients, for example, silicate derivatives such as light silicic acid anhydride, synthetic aluminum silicate, calcium silicate or magnesium aluminate metasilicate; phosphate derivatives such as calcium hydrogenphosphate; carbonates such as calcium carbonate; or sulfates such as calcium sulfate), lubricants (for example, stearic acid; metal stearate derivatives such as calcium stearate or magnesium stearate; talc; waxes such as beeswax or spermaceti; boric acid; adipic acid; sulfate derivatives such as sodium sulfate; glycol; fumaric acid; sodium benzoate; DL-leucine; lauryl sulfate derivatives such as sodium lauryl sulfate or magnesium lauryl sulfate; silicic acid derivatives such as silicic acid anhydride or silicic acid hydrate; and starch derivatives described above), binders (for example, hydroxypropyl cellulose, hydroxypropylmethylcellulose, poly(vinylpyrrolidone), polyethylene glycol and similar compounds described in the above excipients), disintegrators (for example, cellulose derivatives such as low substituted hydroxypropylcellulose, carboxymethylcellulose, calcium carboxymethylcellulose, internally cross-linked sodium carboxymethylcellulose; chemically modified starch/cellulose derivatives such as carboxymethylstarch, sodium carboxymethylstarch; cross-linked polyvinylpyrrolidone; or starch derivatives described above), emulsifiers (for example, colloidal clays such as bentonite or veegum; metal hydroxides such as magnesium hydroxide or aluminum hydroxide; anionic surfactants such as sodium lauryl sulfate or calcium stearate; cationic surfactants such as benzalkonium chloride; or nonionic surfactants such as polyoxyethylene allyl ether, polyoxyethylenesorbitan ester of fatty acids or sucrose ester of fatty acids), stabilizers (for example, parahydroxybenzoates such as methylparaben or propylparaben; alcohols such as chlorobutanol, benzyl alcohol or phenylethyl alcohol; benzalkonium chlorides; phenol derivatives such as phenol or cresol; thimerosal; dehydroacetic acid; or sorbic acid), corrigents (for example, sweetening, souring and flavoring agents all of which are conventionally used), and diluents.

The dose and the dose ratio of 2-acetoxy-5-(α-cyclopropylcarbonyl-2-fluorobenzyl)-4,5,6,7-tetrahydrothieno[3,2-c]pyridine or pharmaceutically acceptable salt thereof, and aspirin, can be widely altered based on several factors such as activity of each compound, and the symptoms, age and body weight of the patients.

Generally, the lower limit of the oral dose (mg drug dose/time) is 0.1 mg (preferably, 1 mg) per time, while the upper limit is 1,000 mg (preferably, 500 mg) per time. The lower and upper limits of intravenous injection are 0.01 mg (preferably, 0.1 mg) and 500 mg (preferably, 250 mg), respectively. They are administered to the adult from 1 to 7 times a day based on the symptoms of the patient, simultaneously or sequentially.

Generally, the dose ratio of 2-acetoxy-5-(α-cyclopropylcarbonyl-2-fluorobenzyl)-4,5,6,7-tetrahydrothieno[3,2-c]pyridine or pharmaceutically acceptable salt thereof, and aspirin, is from 1:500 to 500:1 as their weight ratio.

EXAMPLES

The present invention is described in detail with examples and formulations in the following. However, the claim of the present invention is not restricted to the following description.

Example 1

Inhibitory Activity against Thrombogenesis

As the test animals, male Sprague Dawley rats of 7 weeks old were purchased from SLC Japan and 6 rats per group were used.

2-Acetoxy-5-(α-cyclopropylcarbonyl-2-fluorobenzyl)-4,5,6,7-tetrahydrothieno[3,2-c]pyridine was synthesized according to the method described in the Specification of Japanese Patent Application Publication No. Hei 6-41139 and was used, while aspirin was purchased from Sigma Chemical Co. and was used. Both compounds were suspended in 5% (w/v) gum arabic solution, and were diluted so as to be 1 ml/kg of administration volume and were orally administered.

The inhibitory activities of the compounds against thrombogenesis or thrombus formation were evaluated in the modified arterio-venous shunt thrombosis model in rats, which was described by Umetsu et al. [*Thromb. Haemost.*, 39, 74-83 (1978)].

The shunt tube was prepared as follows; i.e., both sides of a medical silicon tube of 12 cm length [inner diameter: 1.5 mm, outer diameter: 2.5 mm, purchased from KANEKA Medix Co., Ltd] were connected each to a polyethylene tube of 7 cm length [inner diameter: 0.5 mm, outer diameter: 1.0 mm, purchased from Natsume Seisakusho Co., Ltd.] covered with silicon via a medical silicon tube of 0.7 cm length [inner diameter: 1.0 mm, outer diameter: 1.5 mm, KANEKA Medix Co., Ltd] as connector. A surgical suture of 10 cm length was placed in the silicon tube of 12 cm length.

The animal was anesthetized with an intraperitoneal injection of 40 mg/kg of pentobarbital sodium (purchased from Abbott Laboratories Inc.), and the jugular of one side and the carotid of the other side were exposed. The arteriovenous shunt was made by cannulation of a shunt tube filled with heparin solution [30 units/kg, purchased from Fuso Pharmaceutical Co., Ltd] into the carotid and the jugular which had been previously exposed.

The test compounds were orally administered and the blood was started to circulate into the shunt area two hours after-the administration. Thirty minutes after the circulation was started, the shunt tube was removed, and the thrombus adsorbed on the surgical suture was weighed. The results are shown in Table 1. The results in the table are expressed as the average weight±SE (n=6).

TABLE 1

| Compounds | | | |
|---|---|---|---|
| Compound A (mg/kg) | Aspirin (mg/kg) | Thrombus Weight (mg) | Inhibition Rate (%) |
| 0 | 0 | 52.3 ± 1.2 | — |
| 0 | 10 | 46.6 ± 2.8 | 12.3 ± 4.4 |
| 0.3 | 0 | 43.5 ± 2.1 | 17.0 ± 4.1 |
| 0.6 | 0 | 37.5 ± 2.1 | 28.3 ± 4.0 |
| 0.3 | 10 | 30.5 ± 3.5 | 41.8 ± 6.6 |
| 0.6 | 10 | 23.2 ± 3.8 | 55.7 ± 7.2 |

Compound A: 2-Acetoxy-5-(α-cyclopropylcarbonyl-2-fluorobenzyl)-4,5,6,7-tetrahydrothieno[3,2-c]pyridine (Formulation 1)

| Tablets | |
|---|---|
| Compound A | 10.0 mg |
| Aspirin | 12.5 mg |
| Lactose | 175.5 mg |
| Corn starch | 50.0 mg |
| Magnesium stearate | 2.0 mg |
| Total | 250 mg |

The powders in the formula described in the above table are mixed, compressed with a tableting machine and formulated as a tablet containing 250 mg in total. The tablet can be coated with film or sugar, when necessary.

What is claimed is:

1. A method for preventing disease caused by thrombus or embolus, said method consisting of separately administering to a human in need of prevention of said disease:
   (a) 2-acetoxy-5 -(α-cyclopropylcarbonyl-2-fluorobenzyl)-4,5,6,7-tetrahydrothieno[3,2-c]pyridine or a pharmaceutically acceptable salt thereof, and one or more pharmaceutically acceptable excipients, lubricants, binders, disintegrators, emulsifiers, stabilizers, corrigents and/or diluents, and
   (b) aspirin, and one or more pharmaceutically acceptable excipients, lubricants, binders, disintegrators, emulsifiers, stabilizers, corrigents and/or diluents,
   wherein said 2-acetoxy-5 -(α-cyclopropylcarbonyl-2-fluorobenzyl)-4,5,6,7-tetrahydrothieno[3,2-c]pyridine or the pharmaceutically acceptable salt thereof, and aspirin are administered in pharmacologically effective amounts to prevent said disease caused by thrombus or embolus by reducing thrombogenesis or by reducing platelet aggregation in said human, after both (a) and (b) have been administered.

2. The method according to claim 1, wherein the pharmaceutically acceptable salt is 2-acetoxy-5-(α-cyclopropylcarbonyl-2-fluorobenzyl)-4,5,6,7-tetrahydrothieno[3,2-c]pyridine hydrochloride.

3. A method for treating a disease caused by thrombus or embolus, said method consisting of separately administering to a human in need of reduction of thrombogenesis or reduction of platelet aggregation:
   (a) 2-acetoxy-5 -(α-cyclopropylcarbonyl-2-fluorobenzyl)-4,5,6,7-tetrahydrothieno[3,2-c]pyridine or a pharmaceutically acceptable salt thereof, and one or more pharmaceutically acceptable excipients, lubricants, binders, disintegrators, emulsifiers, stabilizers, corrigents and/or diluents, and
   (b) aspirin, and one or more pharmaceutically acceptable excipients, lubricants, binders, disintegrators, emulsifiers, stabilizers, corrigents and/or diluents,
   wherein said 2-acetoxy-5 -(α-cyclopropylcarbonyl-2-fluorobenzyl)-4,5,6,7-tetrahydrothieno[3,2-c]pyridine or the pharmaceutically acceptable salt thereof, and aspirin are administered in pharmacologically effective amounts to treat said disease caused by thrombus or embolus by reducing thrombogenesis or by reducing platelet aggregation in said human, after both (a) and (b) have been administered.

4. The method according to claim 1, wherein said disease caused by thrombus or embolus is a cardiovascular or cerebrovascular disorder.

5. The method according to claim 1, wherein said disease caused by thrombus or embolus is thromboembolism associated with atherosclerosis or diabetes mellitus.

6. The method according to claim 1, wherein said disease caused by thrombus or embolus are unstable angina pectoris, cerebral ischemic insult or restenosis due to angioplasty, endarterectomy or stent therapy.

7. The method according to claim 3, wherein the pharmaceutically acceptable salt is 2-acetoxy-5-(α-cyclopropylcarbonyl-2-fluorobenzyl)-4,5,6,7-tetrahydrothieno[3,2-c]pyridine hydrochloride.

8. A method for treating a patient undergoing stenting or angioplasty consisting of separately administering to said patient:
(a) 2-acetoxy-5 -(α-cyclopropylcarbonyl-2-fluorobenzyl)-4,5,6,7-tetrahydrothieno[3,2-c]pyridine or a pharmaceutically acceptable salt thereof, and one or more pharmaceutically acceptable excipients, lubricants, binders, disintegrators, emulsifiers, stabilizers, corrigents and/or diluents, and
(b) aspirin, and one or more pharmaceutically acceptable excipients, lubricants, binders, disintegrators, emulsifiers, stabilizers, corrigents and/or diluents,
wherein said 2-acetoxy-5 -(α-cyclopropylcarbonyl-2-fluorobenzyl)-4,5,6,7-tetrahydrothieno[3,2-c]pyridine or the pharmaceutically acceptable salt thereof, and aspirin are administered in pharmacologically effective amounts to reduce the incidence or severity of restenosis in said patient undergoing stenting or angioplasty, after both (a) and (b) have been administered.

9. The method according to claim 8, wherein the pharmaceutically acceptable salt is 2-acetoxy-5-(α-cyclopropylcarbonyl-2-fluorobenzyl)-4,5,6,7-tetrahydrothieno[3,2-c]pyridine hydrochloride.

10. The method according to claim 2, wherein the 2-acetoxy-5-(α-cyclopropylcarbonyl-2-fluorobenzyl)-4,5,6,7-tetrahydrothieno[3,2-c]pyridine hydrochloride, and aspirin are administered at separate times.

11. The method according to claim 1, wherein the pharmacologically effective amounts are pharmacologically effective amounts for said 2-acetoxy-5-(α-cyclopropylcarbonyl-2-fluorobenzyl)-4,5,6,7-tetrahydrothieno[3,2-c]pyridine hydrochloride and aspirin, individually.

12. The method according to claim 3, wherein said disease caused by thrombus or embolus is a cardiovascular disorder.

13. The method according to claim 3, wherein said disease caused by thrombus or embolus is thromboembolism associated with atherosclerosis or diabetes mellitus.

14. The method according to claim 3, wherein said diseases caused by thrombus or embolus are unstable angina pectoris, or restenosis due to angioplasty, endarterectomy or stent therapy.

15. A method for reducing event rate of diseases caused by thrombus or embolus, said method consisting of separately administering to a human in need of reduction of said event rate of said diseases:
(a) 2-acetoxy-5 -(α-cyclopropylcarbonyl-2-fluorobenzyl)-4,5,6,7-tetrahydrothieno[3,2-c]pyridine or a pharmaceutically acceptable salt thereof, and one or more pharmaceutically acceptable excipients, lubricants, binders, disintegrators, emulsifiers, stabilizers, corrigents and/or diluents, and
(b) aspirin, and one or more pharmaceutically acceptable excipients, lubricants, binders, disintegrators, emulsifiers, stabilizers, corrigents and/or diluents,
wherein said 2-acetoxy-5 -(α-cyclopropylcarbonyl-2-fluorobenzyl)-4,5,6,7-tetrahydrothieno[3,2-c]pyridine or the pharmaceutically acceptable salt thereof, and aspirin are administered in pharmacologically effective amounts to said reduce event rate of said diseases caused by thrombus or embolus by reducing thrombogenesis or by reducing platelet aggregation in said human, after both (a) and (b) have been administered.

16. The method according to claim 15, wherein the pharmaceutically acceptable salt is 2-acetoxy-5-(α-cyclopropylcarbonyl-2-fluorobenzyl)-4,5,6,7-tetrahydrothieno[3,2-c]pyridine hydrochloride.

17. The method according to claim 15, wherein said diseases caused by thrombus or embolus are selected from the group consisting of: diseases induced by platelet aggregation, cardiovascular disorders, cerebrovascular disorders, and thromboembolism caused by thromboembolization.

18. The method according to claim 15, wherein said diseases caused by thrombus or embolus are selected from the group consisting of: stable or unstable angina pectoris, thromboembolism associated with atherosclerosis or diabetes mellitus, recurrent embolism after degradation of original thrombus, embolism, ischemia-induced dementia, peripheral arteriopathy, thromboembolization associated with hemodialysis or atrial fibrillation, and thromboembolization in vascular prosthesis or in bypass between the aorta and the coronary artery.

19. The method according to claim 15, wherein said diseases caused by thrombus or embolus are diseases selected from the group consisting of stable or unstable angina pectoris, cerebral ischemic insult, and restenosis due to angioplasty, endarterectomy or stent therapy.

20. A method for reducing thrombotic cardiovascular or thrombotic cerebrovascular events in a human in need of reduction of said events, said method consisting of separately administering:
(a) 2-acetoxy-5-(α-cyclopropylcarbonyl-2-fluorobenzyl)-4,5,6,7-tetrahydrothieno[3,2-c]pyridine or a pharmaceutically acceptable salt thereof, and one or more pharmaceutically acceptable excipients, lubricants, binders, disintegrators, emulsifiers, stabilizers, corrigents and/or diluents, and
(b) aspirin, one or more pharmaceutically acceptable excipients, lubricants, binders, disintegrators, emulsifiers, stabilizers, corrigents and/or diluents,
wherein said 2-acetoxy-5-(α-cyclopropylcarbonyl-2-fluorobenzyl)-4,5,6,7-tetrahydrothieno[3,2-c]pyridine or the pharmaceutically acceptable salt thereof, and aspirin are administered in pharmacologically effective amounts to reduce thrombotic cardiovascular or thrombotic cerebrovascular events by reducing thrombogenesis or by reducing platelet aggregation in said human, after both (a) and (b) have been administered.

21. The method according to claim 20, wherein the pharmaceutically acceptable salt is 2-acetoxy-5-(α-cyclopropylcarbonyl-2-fluorobenzyl)-4,5,6,7-tetrahydrothieno[3,2-c]pyridine hydrochloride.

22. The method according to claim 20, wherein said method reduces thrombotic cardiovascular events in said human.

23. The method according to claim 20, wherein said method reduces thrombotic cerebrovascular events in said human.

24. A method for reducing thrombogenesis or reducing platelet aggregation in a human, said method consisting of separately administering to said human:
(a) 2-acetoxy-5-(α-cyclopropylcarbonyl-2-fluorobenzyl)-4,5,6,7-tetrahydrothieno[3,2-c]pyridine or a pharmaceutically acceptable salt thereof, and one or more pharmaceutically acceptable excipients, lubricants, binders, disintegrators, emulsifiers, stabilizers, corrigents and/or diluents, and (b) aspirin, and one or more pharmaceutically acceptable excipients, lubricants, binders, disintegrators, emulsifiers, stabilizers, corrigents and/or diluents, wherein said 2-acetoxy-5-(α-cyclopropylcarbonyl-2-fluorobenzyl)-4,5,6,7-tetrahydrothieno[3,2-c]pyridine or the pharmaceutically acceptable salt thereof, and aspirin are administered in pharmacologically effective amounts to reduce thrombogenesis or reduce platelet aggregation in said human, after both (a) and (b) have been administered.

25. The method according to claim 24, wherein the pharmaceutically acceptable salt is 2-acetoxy-5-(α-cyclopropylcarbonyl-2-fluorobenzyl)-4,5,6,7-tetrahydrothieno[3,2-c]pyridine hydrochloride.

26. The method according to claim 25, wherein the 2-acetoxy-5-(α-cyclopropylcarbonyl-2-fluorobenzyl)-4,5,6,7-tetrahydrothieno[3,2-c]pyridine hydrochloride, and aspirin are administered at separate times.

* * * * *

UNITED STATES PATENT AND TRADEMARK OFFICE
CERTIFICATE OF CORRECTION

PATENT NO. : 8,569,325 B2  
APPLICATION NO. : 12/006546  
DATED : October 29, 2013  
INVENTOR(S) : Fumitoshi Asai et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 968 days.

Signed and Sealed this  
Thirteenth Day of May, 2014

Michelle K. Lee  
*Deputy Director of the United States Patent and Trademark Office*